US006986730B1

(12) United States Patent
Hoekstra

(10) Patent No.: US 6,986,730 B1
(45) Date of Patent: *Jan. 17, 2006

(54) CONTINUOUS WEB OF BREATHER POUCHES AND AUTOMATED METHOD OF PACKAGING MEDICAL DEVICES UTILIZING SUCH POUCHES

(75) Inventor: Todd Hoekstra, 2285 Copperfield Dr., Mendota Heights, MN (US) 55120

(73) Assignee: Todd Hoekstra, Mendota Heights, MN (US)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/932,745

(22) Filed: Aug. 17, 2001

(51) Int. Cl.
B31B 1/16 (2006.01)

(52) U.S. Cl. .................. 493/224; 206/439; 206/363

(58) Field of Classification Search ............... 206/439, 206/438, 820, 363; 493/922, 204, 224, 228, 493/240
See application file for complete search history.

(56) References Cited

U.S. PATENT DOCUMENTS

| 4,226,410 A | * | 10/1980 | McIntosh et al. ............ 493/410 |
| 4,236,731 A | * | 12/1980 | Hektoen ........................ 462/6 |
| 4,947,620 A |  | 8/1990 | Carter .......................... 53/425 |
| 4,962,856 A |  | 10/1990 | Carter ......................... 206/439 |
| 5,033,252 A |  | 7/1991 | Carter .......................... 53/425 |
| 5,052,558 A |  | 10/1991 | Carter ......................... 206/439 |
| 5,178,267 A |  | 1/1993 | Grabenkort et al. ......... 206/210 |
| 5,178,277 A |  | 1/1993 | Brown et al. ................ 206/439 |
| 5,217,772 A |  | 6/1993 | Brown et al. ................. 428/40 |
| 5,220,769 A |  | 6/1993 | Brown et al. ................. 53/453 |
| 5,536,356 A |  | 7/1996 | Stuerzel ....................... 156/514 |
| 5,571,361 A |  | 11/1996 | Stuerzel ....................... 156/252 |
| 5,590,778 A |  | 1/1997 | Dutchik ....................... 206/439 |
| 5,715,943 A | * | 2/1998 | Thompson, Jr. ............ 206/363 |
| 5,830,547 A |  | 11/1998 | MacKenzie et al. ....... 428/36.1 |
| 5,868,244 A | * | 2/1999 | Ivanov et al. ............... 206/439 |
| 5,949,032 A | * | 9/1999 | Wurzburger ................ 181/131 |
| 5,976,299 A |  | 11/1999 | Ivey ............................ 156/270 |
| 6,034,008 A |  | 3/2000 | Lim et al. ................... 442/334 |
| 6,117,505 A | * | 9/2000 | Weiss et al. ................ 428/35.2 |
| 6,228,324 B1 |  | 5/2001 | Hasegawa et al. ............ 422/30 |
| 6,419,392 B1 |  | 7/2002 | Baker .......................... 383/37 |
| 6,449,925 B1 | * | 9/2002 | Otsu et al. .................... 53/428 |

OTHER PUBLICATIONS

Product Bulletin, "Tyvek® 2FS™. . . A Better Alternative to Paper for Form/Fill/Seal Applications," Jun. 1999.
DuPont Medical Packaging, "Tyvek Technical Information & Tips," www,tyvek.com, Jun. 1, 2001.
Automated Packagiing Systems,"Precision™ AutoLabel™" brochure, 1997.
Automated Packaging Systems, "H-100 E Autobag®" brochure, 1998.
Automated Packaging Systems, "Accu-Count® Advantage Autobag®"brochure, 1997.
Automated Packaging Systems, "HS-100™ Excel® Autobag®"brochure, 1997.
Automated Packaging Systems, "Automatic Hand Load Bagger HB-85 PaceSetter™ Plus" brochure, 2001.

(Continued)

Primary Examiner—Rinaldi I. Rada
Assistant Examiner—John Paradiso
(74) Attorney, Agent, or Firm—Watts Hoffmann Co., L.P.A.

(57) ABSTRACT

A continuous web of breather pouches separated by detachment lines and automated method of packaging medical devices using such a continuous web.

25 Claims, 5 Drawing Sheets

OTHER PUBLICATIONS

Automated Packaging Systems, "PaceSetter™ Autobag®" brochure, 1997.
Automated Packaging Systems, "SPrint™ SidePouch™" brochure, 1998.
Automated Packaging Systems, "MAXIMIZER™ Conveyer Autobag®" brochure.
Automated Packaging Systems, "Accu-Count® 118/124 Autobag®" brochure.
Automated Packaging Systems, "Accu-Scale® 200 Autobag®" brochure.
Automated Packaging Systems, "Accu-Count® DAC-1000 Autobag®" brochure.
Automated Packaging Systems, "Accu-Count® 107" brochure.
Advanced Poly-Packaging, Inc. "T-1000 Advanced Poly-Bagger™" brochure, Jan. 1996.
Adavanced Poly-Packaging, Inc. "Roll-a-Print™ Stand-alone Printer & Seal-a-Print™ Printer-Bagger" brochure, Nov. 1996.
Advanced Poly-Packaging, Inc. "Ultra-Feed™ 5000 Product In-Feed Conveyor" brochure, Nov. 1996.
Advanced Poly-Packaging, Inc. "Flip-Series™ Scale, Model 810" brochure, Nov. 1996.
Sharp Packaging Systems, Inc., "E-Z Bags®" brochure.
Sharp Packaging Systems, Inc., "Lower Your Total Packaging Costs with the Dependable BPS-2™" brochure.
Sharp Packaging Systems, Inc., "The Sharp Choice: The innovative manufacturer of flexible packaging systems—pre-opened bags on a roll and bagging machinery" brochure.
Advanced Poly•Packaging, Inc., Product Catalog, 2001.

* cited by examiner

CONTINUOUS WEB OF BREATHER POUCHES AND AUTOMATED METHOD OF PACKAGING MEDICAL DEVICES UTILIZING SUCH POUCHES

FIELD OF INVENTION

The invention relates to pouches for packaging medical devices and methods of packaging medical devices. More particularly, the invention relates to display pouches useful for the sterilization packaging of medical devices and automated methods for the sterilization packaging of medical devices.

BACKGROUND

Packaging pouches for medical devices typically comprises a transparent thermoplastic sheet, such as polycoated polyester, polycoated nylon, polyethylene or polypropylene film, thermally sealed along the periphery to a gas permeable microbial barrier layer, such as medical grade paper or spunbound polyolefin, hereinafter referenced as a breather pouch.

One of the more popular materials for use as the gas permeable microbial barrier layer is a spunbonded polyolefin material known as TYVEK® (a registered trademark of E.I. du Pont de Nemours and Company). TYVEK® spunbonded polyolefin has been in use for a number of years as a material for sterile packaging applications because of its light weight, excellent strength, good microbial barrier properties, and reasonable permeability to sterilization gases such a ethylene oxide and hydrogen peroxide.

Breather pouches allow medical devices retained within the pouch to be sterilized after the device has been sealed within the pouch by a process known as medical sterilization packaging. Briefly, medical sterilization packaging is a packaging method which involves placement of the medical device within a breather pouch, thermally sealing the breather pouch, and exposing the pouch to a sterilizing gas, such as ethylene oxide or hydrogen peroxide. The sterilizing gas will penetrate through the gas permeable layer of the breather pouch and sterilize the medical device within the pouch without disturbing the sealed condition of the pouch.

Breather pouches are generally provided as stacks of single pouches having one open end to manufacturers of medical devices. The medical devices are placed within each pouch by hand and the open end of the pouch thermally sealed by hand. Such hand packaging of medical devices is slow, labor intensive and expensive. Hence, a need exists for an automated method of packaging medical devices into breather pouches.

SUMMARY OF THE INVENTION

A first aspect of the invention is a longitudinally continuous web defining a plurality of breather pouches.

A first embodiment of the first aspect of the invention (hereinafter referenced as a top-feed web) is a web having superimposed first and second layers sealingly engaged along the lateral sides. The first layer is a gas permeable microbial barrier layer. The second layer is a thermoplastic gas impermeable layer. Sequential pouches are separated by a laterally extending line of weakness in one of the layers paired with a laterally extending line of separation in the other layer.

A second embodiment of the first aspect of the invention (hereinafter referenced as a side-feed web) is a longitudinally continuous web having superimposed first and second layers sealingly engaged along one lateral end. The first layer is a gas permeable microbial barrier layer. The second layer is a thermoplastic gas impermeable layer. Sequential pouches are separated by longitudinally spaced and laterally extending paired lines of weakness in the first and second layers. The first and second layers are also sealed along a pair of laterally extending seal lines located proximate each paired line of weakness. The individual laterally extending seal lines in each pair of laterally extending seal lines are separated by a paired lines of weakness.

A second aspect of the invention is an automated method of packaging a medical device using a continuous web defining a plurality of breather pouches.

A first embodiment of the second aspect of the invention uses the top-feed web of the first aspect of the invention.

The first embodiment of the second aspect of the invention includes the steps of (i) obtaining a top-feed web of breather pouches, (ii) automatically conveying the web in a machine direction until the leading pouch is positioned at a fill location, (iii) automatically transversely separating the first and second layers of the leading pouch along the second end of the leading pouch so as to open the second end of the leading pouch, (iv) placing a medical device within the retention chamber defined by the leading pouch through the open second end of the leading pouch, (v) sealing the second end of the leading pouch with the medical device retained within the retention chamber, (vi) automatically detaching the leading pouch from the trailing pouch along the line of weakness in the first layer between the leading pouch and the immediately trailing pouch after step (iv), and (vii) repeating steps (ii) through (vi) for subsequent pouches in the web.

A second embodiment of the second aspect of the invention uses the side-feed web of the second aspect of the invention.

The second embodiment of the second aspect of the invention includes the steps of (i) obtaining a side-feed web of breather pouches, (ii) automatically conveying the web in a machine direction until the leading pouch is positioned at a fill location, (iii) automatically transversely separating the first and second layers of the web along the first lateral side of the web so as to provide access to the retention chamber defined by the leading pouch, (iv) placing a medical device within the retention chamber defined by the leading pouch through the open lateral side of the web, (v) sealing the leading pouch along the lateral side of the web with the medical device retained within the retention chamber, (vi) automatically detaching the leading pouch from the trailing pouch along the lines of weakness in the first and second layers between the leading pouch and the immediately trailing pouch after step (iv), and (vii) repeating steps (ii) through (vi) for subsequent pouches in the web.

DETAILED DESCRIPTION OF THE INVENTION INCLUDING A BEST MODE

Nomenclature
10 Continuous Web
11 First Lateral Side of Continuous Web
12 Second Lateral Side of Continuous Web
20 Gas Permeable Microbial Barrier Layer
30 Thermoplastic Gas Impermeable Layer
40 Line of Detachment
41 Line of Weakness Through Gas Permeable Microbial Barrier Layer
42' Line of Separation Through Thermoplastic Gas Impermeable Layer
42" Line of Weakness Through Thermoplastic Gas Impermeable Layer
50 Processing Margin
51 Line of Attachment
52 Forward Edge of Processing Margin
100 Individual Breather Pouch
101 Leading Breather Pouch
102 Immediately Trailing Breather Pouch
111 First Side of Pouch
112 Second Side of Pouch
113 First End of Pouch
114 Second End of Pouch
119 Retention Chamber
121 Seal Line Along First Side of Pouch
122 Seal Line Along Second Side of Pouch
123 Seal Line Along First End of Pouch
124 Seal Line Along Second End of Pouch
130 Peel Opening
200 Medical Device
x Longitudinal Down-Web Direction
y Latitudinal Cross-Web Direction Definitions As utilized herein, including the claims, the phrase "gas permeable microbial barrier" means permeable to sterilizing gases such as ethylene oxide and hydrogen peroxide and impermeable to microbial contaminants including bacteria, viruses, and spores.

As utilized herein, including the claims, the phrase "line of separation", when used in connection with a layer of the continuous web, means a line of continuous disconnection extending across the entire lateral width of the layer (i.e., complete separation) or extending across the majority of the lateral width of the layer leaving a connected margin at each side of the web (i.e., a central opening).

As utilized herein, including the claims, "tear strength" means the force required to separate a sheet along a line of weakness, which divides the sheet into two sections. Tear strength is measured with a tension measurement device such as a DFGS series Digital Force Gauge available from John Chatillon & Sons, Inc. of Greensboro, N.C. Briefly, the test is conducted by placing one section of the sheet into the clamp of the tension measuring device, gripping the other section by the thumb and pointer finger, and slowly pulling away from the clamp until the sheet tears along the line of weakness.

Continuous Web of Breather Pouches

A first aspect of the invention is a longitudinally continuous web 10 containing a plurality of breather pouches 100 configured and arranged for use with automated packaging systems (not shown) in the sterilization packaging of medical devices 200.

Figure 1:
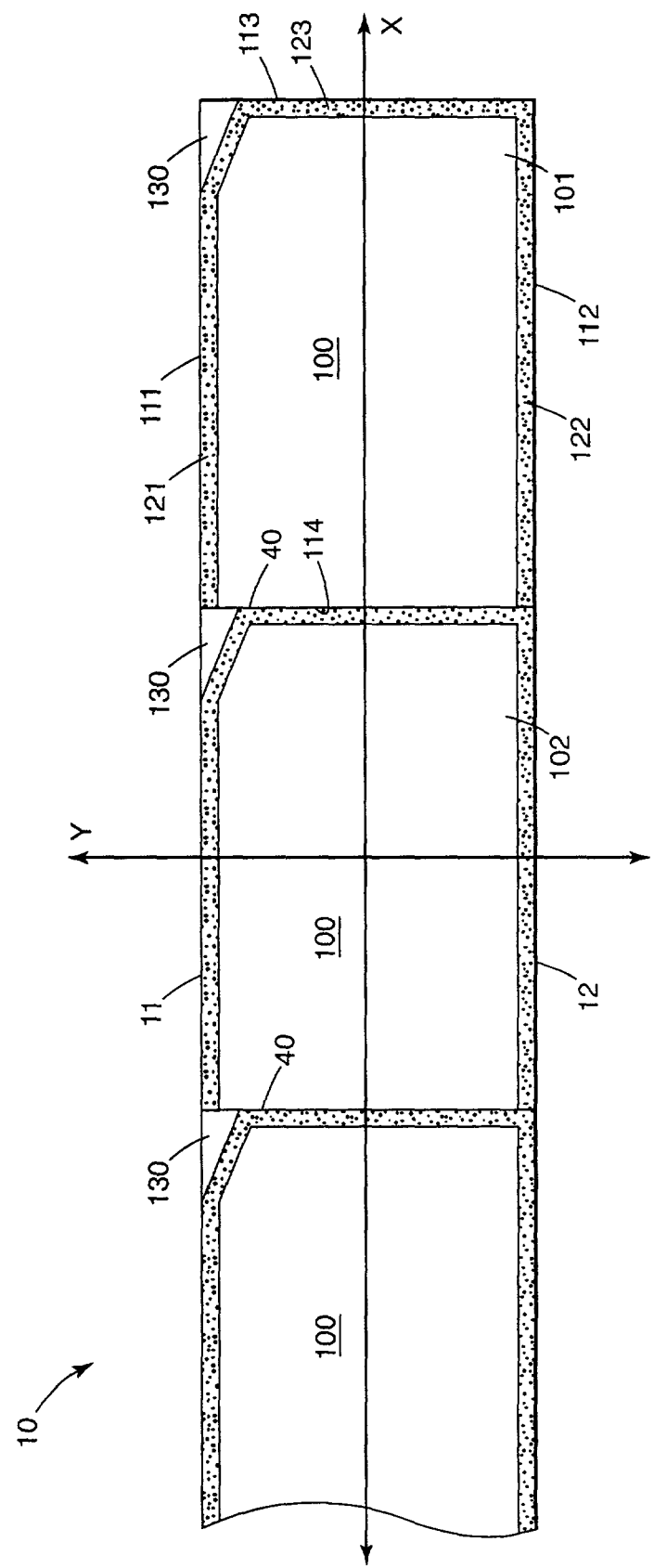
FIG. 1 is a top view of the leading end of one embodiment of a top-feed continuous web of breather pouches.
Figure 2:
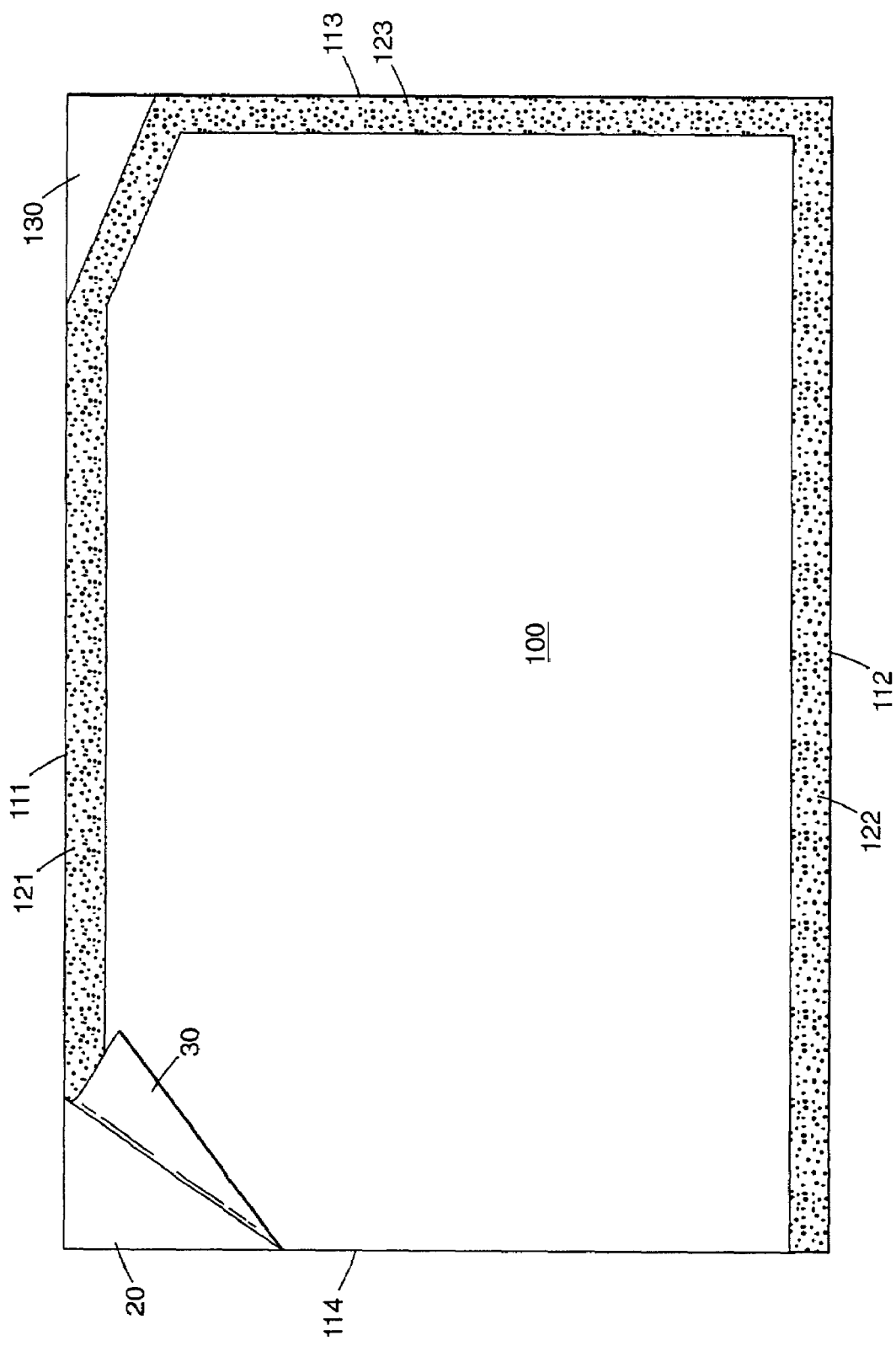
FIG. 2 is a top view of an individual breather pouch separated from the continuous web of breather pouches shown in FIG. 1, with a corner of the thermoplastic gas impermeable layer lifted to reveal the gas permeable microbial barrier layer.
Figure 3:
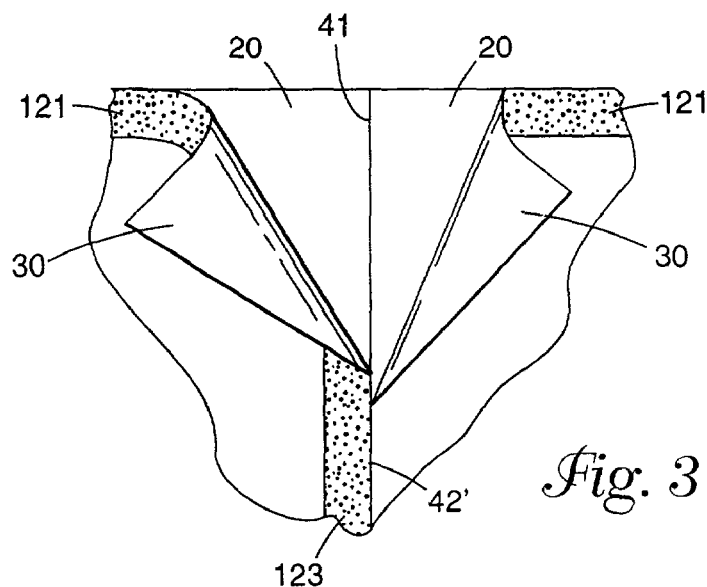
FIG. 3 is an enlarged top view of a portion of the continuous web of breather pouches shown in FIG. 1, with the thermoplastic gas impermeable layer separated along the line of weakness and lifted from supplementary corners on sequential pouches to reveal the line of weakness in the gas permeable microbial barrier layer between the sequential pouches.
Figure 4:
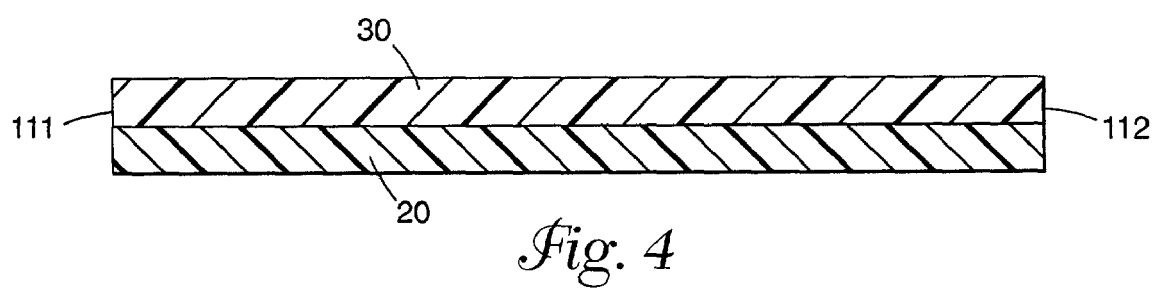
FIG. 4 is an enlarged end view of the open end of the breather pouch shown in FIG. 2.
Figure 5:
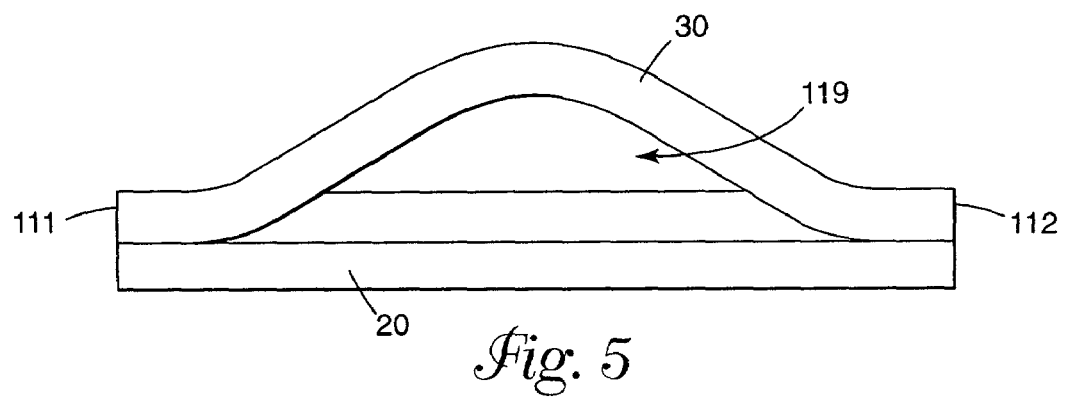
FIG. 5 is an end view of the open end of the breather pouch shown in FIG. 4 with the layers separated to allow access to the retention chamber defined by the pouch.
Figure 6:
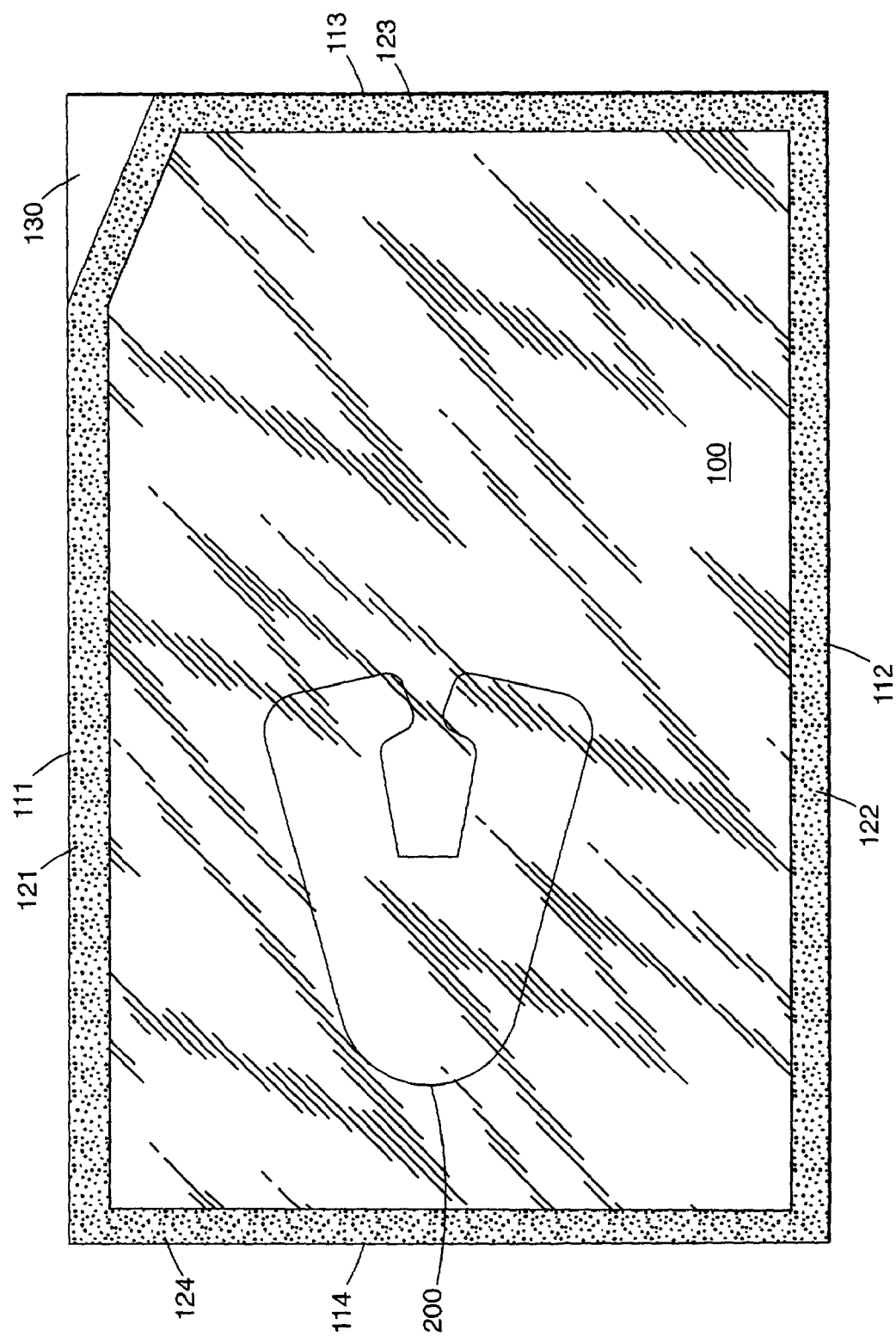
FIG. 6 is a top view of the breather pouch shown in FIG. 2 after placement of a medical device within the retention chamber and sealing of the open end of the pouch.

Referring to FIG. 1, a first embodiment of the first aspect of the invention is a top-feed continuous web 10 having superimposed first 20 and second 30 layers sealingly engaged proximate the lateral sides 11 and 12 along longitudinally extending seal lines 121 and 122 respectively. The web 10 includes a series of longitudinally spaced and laterally extending lines of detachment 40 through the web 10. Each line of detachment 40 includes a line of weakness 41 through the first layer 20 paired with a line of separation 42' through the second layer 30. Alternatively, each line of detachment 40 can provide the line of weakness through the second layer 30 and the line of separation through the first layer 20. For purposes of providing a lucid disclosure, the balance of the disclosure shall be based upon the option in which each line of detachment 40 includes a line of weakness 41 through the first layer 20 paired with a line of separation 42' through the second layer 30.

The first 20 and second 30 layers are also sealingly engaged along a laterally extending seal line 123 located proximate but longitudinally offset from each line of detachment 40. The laterally extending seal line 123 extends between and connects the longitudinally extending seal lines 121 and 122 to define a retention chamber 119 in each pouch 100 which is sealed along both sides and one end of the pouch 100 (i.e., both sides 111 and 112 and one end 123 or 124) and open at the fourth side of the pouch 100 (i.e., the other end 123 or 124). The line of detachment 40 separates sequential pouches 100 in the web 10.

The first layer 20 is a gas permeable microbial barrier layer, such as medical grade paper or medical grade TYVEK® available from E.I. duPont de Numours and Company. The second layer 30 is a thermoplastic gas impermeable layer, such as a polycoated polyester, polycoated nylon, polyethylene or polypropylene film. The second layer 30 is preferably transparent so that the medical device 200 packaged within the pouch 100 can be viewed by medical personnel (not shown).

Each paired line of weakness 41 through the first layer 20 and line of separation 42' through the second layer 30 are preferably transversely superimposed. The line of weakness 41 is preferably a line of perforation formed with a perforating die (not shown) before or after the first 20 and second 30 layers are superimposed. A perforated line of weakness 41 can also be formed using a laser such as described in U.S. Pat. Nos. 5,444,035 and 5,556,826. The line of separation 42' in the second layer 30 is preferably formed after the first 20 and second 30 layers are superimposed and the seal lines 121, 122 and 123 formed, by laterally kiss-cutting the second layer 30 at the desired locations.

The lines of weakness 41 are individually comprised of a line along which the material is thinned or perforated. The tear strength of the lines of weakness 41 must be selected to provide a tear strength in the first layer 20 sufficient to prevent accidental and unintentional separation along the line of weakness 41, while allowing clean and consistent separation of the first layer 20 along the line of weakness 41 at the desired time during the automated packaging process. When the line of weakness 41 is created by a line of thinned material, the desired tear strength is controlled by controlling the thickness of material along the line of weakness 41. When the line of weakness 41 is created by perforations, the desired tear strength is controlled by controlling the hole density (i.e., holes per centimeter) and hole:land ratio (i.e., # of holes:# of lands).

TYVEK® is very tough material with extraordinarily high tear strength. In order to ensure a clean tear with an acceptable tear strength along the line of weakness 41 in the first layer 20 when the first layer 20 is constructed of TYVEK®, the force required to tear the first layer 20 along the line of weakness 41 should be no more than 10%, preferably no more than 5% and most preferably no more than 2% of the force required to laterally tear the first layer 20 without the presence of a line of weakness 41. Generally, such tear strengths along the line of weakness 41 in a first layer 20 constructed from TYVEK® can be achieved with a hole density of between about 0.4 to 0.6 holes per centimeter, and hole:land ratio of between about 15:1 to 25:1, preferably about 20:1. A perforated line of weakness 41 in the first layer 20 with a hole density and hole:land ratio outside these ranges tends to produce a line of weakness 41 which (i) prematurely separates, (ii) does not separate cleanly along the perforated line of weakness 41, (iii) requires excessive force to achieve separation causing periodic failure during packaging, and (iv) has holes (not shown) which are so long that the first layer 20 will occasionally fold, crease and/or wrinkle at the hole (not shown) and cause periodic failure during packaging and/or a failed seal.

The seal lines 121, 122, and 123 must be able to prevent the passage of microbes through the seal (e.g., no puckering of the first 20 or second 30 layer of material along the seal line 121, 122, or 123 and a seal line width of at least ⅜ inch). Seal lines 121, 122 and 123 may be formed by thermal or ultrasonic techniques conventionally employed to seal breather pouches used in medical sterilization packaging.

Seal lines 121, 122 and 123 define a retention chamber 119 in each pouch 100. The seal lines 121 and 123 or 122 and 123 should be laterally offset from the side 11 or 12 and end 13 of the web 10 in at least one corner (unnumbered) to form a corner peel opening 130 for facilitating separation of the layers 20 and 30 by medical personnel (not shown) in order to gain access to the sterile medical device 200 packaged within the retention chamber 119 of the pouch 100.

The continuous web 10 may be wound onto a core (not shown) to form a roll (not shown) or folded back upon itself at regular intervals along the laterally extending line of detachment 40 (e.g., each laterally extending line of detachment 40, every other laterally extending line of detachment 40, every tenth extending line of detachment 40, etc.) to form a pleated stack (not shown).

Figure 7:
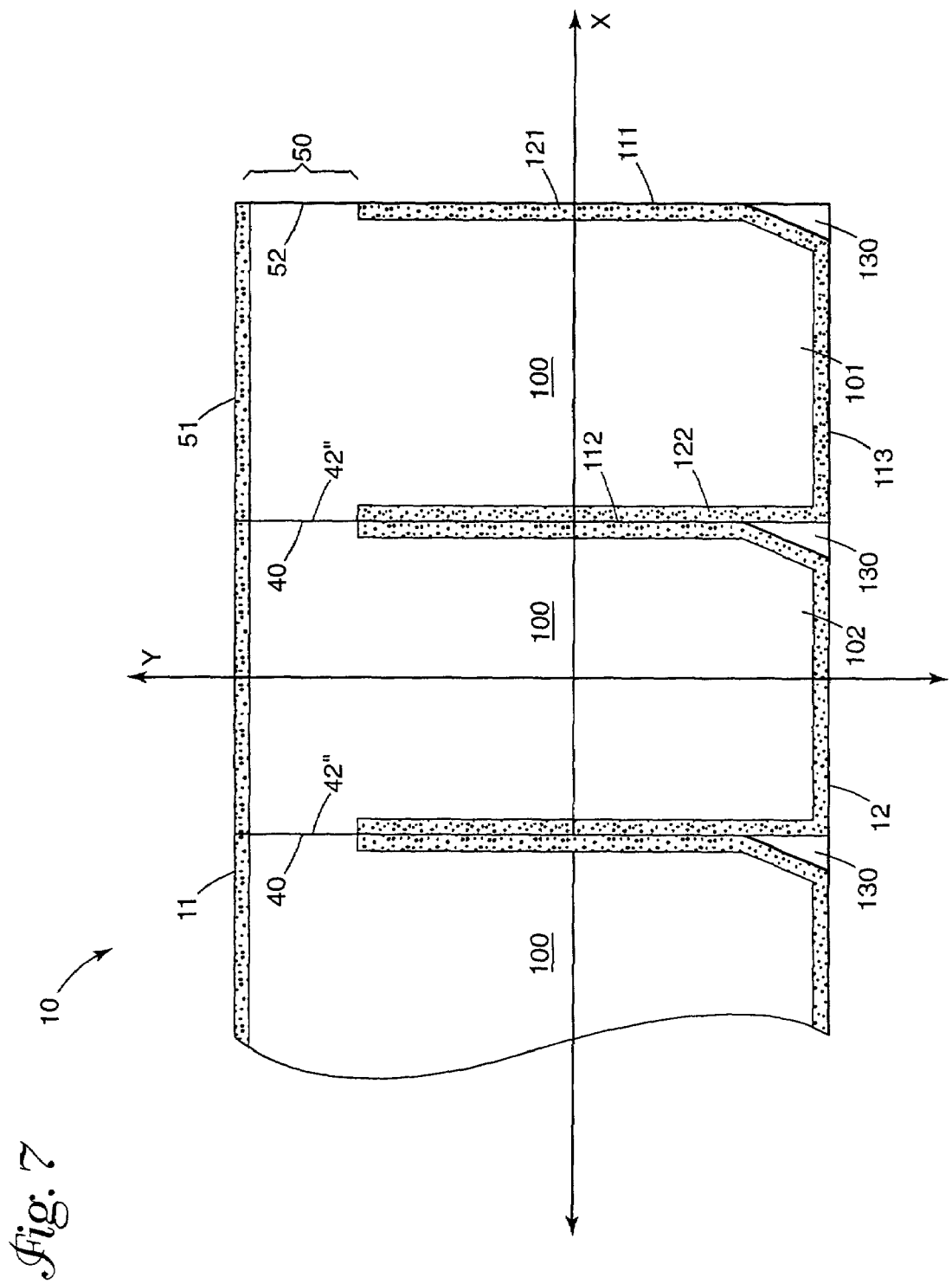
FIG. 7 is a top view of the leading end of one embodiment of a side-feed continuous web of breather pouches.

Referring to FIG. 7, a second embodiment of the first aspect of the invention is a side-feed continuous web 10 having superimposed first 20 and second 30 layers sealingly engaged proximate one lateral side 12 along a longitudinal seal line 123. The web 10 includes a series of longitudinally spaced and laterally extending lines of detachment 40 through the web 10. Each line of detachment 40 includes a line of weakness 41 through the first layer 20 paired with a line of weakness 42" through the second layer 30. The first 20 and second 30 layers are also sealingly engaged along laterally extending seal lines 121 and 122 located proximate each line of detachment 40 with the individual laterally extending seal lines 121 and 122 in each pair of laterally extending seal lines 121 and 122 separated by a line of detachment 40. The longitudinally extending seal line 123 extends between and connects the laterally extending seal lines 121 and 122 to define a retention chamber 119 in each pouch 100 which is sealed along both sides and one end of the pouch 100 (i.e., both sides 111 and 112 and one end 123 or 124) and open at the other end of the pouch 100 (i.e., the other end 123 or 124). The lines of detachment 40 separate sequential pouches 100 in the web 10.

A processing margin 50 with an opening in the forward edge 52 of the margin 50 is provided along the first lateral side 11 of the web 10, as is typically employed with side-feed continuous webs of polyethylene and polypropylene bags, for purposes of allowing the web 10 to be suspended along a horizontal rail (not shown) on an automatic side-feed packaging machine (not shown).

As with the first embodiment of the web 10, the first layer 20 is a gas permeable microbial barrier layer, such as medical grade paper or medical grade TYVEK® available from E.I. dupont de Numours and Company, and the second layer 30 is a thermoplastic gas impermeable layer, such as a polycoated polyester, polycoated nylon, polyethylene or polypropylene film. The second layer 30 is preferably transparent so that the medical device 200 packaged within the pouch 100 can be viewed by medical personnel (not shown).

Each paired line of weakness 41 through the first layer 20 and line of weakness 42" through the second layer 30 are preferably transversely superimposed, with the lines of weakness 41 and 42" simultaneously formed in both layers 20 and 30 utilizing a single die (not shown) after the first 20 and second 30 layers are superimposed. A perforated line of weakness 41 and/or 42" can also be formed using a laser such as described in U.S. Pat. Nos. 5,444,035 and 5,556,826.

The lines of weakness 41 and 42" are individually comprised of a line along which the material of each layer 20 and 30 is thinned or perforated. The tear strength of the lines of weakness 41 and 42" must be selected to provide a tear strength in the respective layer 20 or 30 sufficient to prevent accidental and unintentional separation along the line of weakness 41 or 42", while allowing clean and consistent separation of the layers 20 and 30 along the respective line of weakness 41 or 42" at the desired time during the automated packaging process. When the line of weakness 41 or 42" is created by a line of thinned material, the desired tear strength is controlled by controlling the thickness of material along the line of weakness 41 or 42". When the line of weakness 41 or 42" is created by perforations, the desired tear strength is controlled by controlling the hole density (i.e., holes per centimeter) and hole:land ratio (i.e., # of holes:# of lands).

TYVEK® is very tough material with extraordinarily high tear strength. In order to ensure a clean tear with an acceptable tear strength along the line of weakness 41 in the first layer 20 when the first layer 20 is constructed of TYVEK®, the force required to tear the first layer 20 along the line of weakness 41 should be no more than 10%, preferably no more than 5% and most preferably no more than 2% of the force required to laterally tear the first layer 20 without the presence of a line of weakness 41. Generally, such tear strengths along the line of weakness 41 in a first layer 20 constructed from TYVEK® can be achieved with a hole density of between about 0.2 to 0.6 holes per centimeter, and hole:land ratio of between about 15:1 to 50:1. A perforated line of weakness 41 in the first layer 20 with a hole density and hole:land ratio outside these ranges tends to produce a line of weakness 41 which (i) prematurely separates, (ii) does not separate cleanly along the perforated line of weakness, (iii) requires excessive force to achieve separation causing periodic failure during packaging, and (iv) has holes (not shown) which are so long that the first layer 20 will occasionally fold, crease and/or wrinkle at the hole (not shown) and cause periodic failure during packaging and/or a failed seal.

Polycoated polyester, polycoated nylon, polyethylene and polypropylene have relatively low tear strength compared to TYVEK®. In order to ensure a clean tear along the line of weakness 42" in the second layer 30 when the second layer 30 is constructed of polycoated polyester, polycoated nylon, polyethylene or polypropylene, the force required to laterally tear the second layer 30 along the line of weakness 42" should be no more than 80%, preferably no more than 50% and most preferably no more than 30% of the force required to laterally tear the second layer 30 without the presence of a line of weakness 42". Generally, such tear strengths along the line of weakness 42" in a second layer 30 constructed from polycoated polyester, polycoated nylon, polyethylene or polypropylene can be achieved over a wider range of hole density and hole:land ratios than that necessary for the first layer 20. Hence, it is preferred to simply perforate both the first 20 and second 30 layers with a single perforating dye (not shown) with the hole do density and hole:land ratio set within the ranges acceptable for the first layer 20.

The seal lines 121, 122 and 123 must be able to prevent the passage of microbes through the seal (e.g., no puckering of the first 20 or second 30 layer of material along the seal line and a seal line width of at least ⅜ inch). Seal lines 121, 122 and 123 may be formed by thermal or ultrasonic techniques conventionally employed to seal breather pouches used in medical sterilization packaging.

Seal lines 121, 122 and 123 define a retention chamber 119 in each pouch 100. The seal lines 121 and 123 or 122 and 123 should be laterally offset from the side 11 or 12 and end 13 of the web 10 in at least one corner (unnumbered) to form a corner peel opening 130 for facilitating separation of the layers 20 and 30 by medical personnel (not shown) in order to gain access to the sterile medical device 200 packaged within the retention chamber 119 of the pouch 100.

The continuous web 10 may be wound onto a core (not shown) to form a roll (not shown) or folded back upon itself at regular intervals along the laterally extending line of detachment 40 (e.g., each laterally extending line of detachment 40, every other laterally extending line of detachment 40, every tenth extending line of detachment 40, etc.) to form a pleated stack (not shown).

Automated Method of Packaging Medical Devices Within Breather Pouches

A second aspect of the invention is an automated method of packaging a medical device 200 in a breather pouch 100 using the continuous web 10 of the pouches 100.

A first embodiment of the second aspect of the invention uses the first embodiment of the first aspect of the invention (i.e., a top-feed continuous web 10).

The first embodiment of the second aspect of the invention includes the steps of:
(i) obtaining a top-feed web 10 of breather pouches 100, (ii) automatically conveying the web 10 in a machine direction x until the leading pouch 101 is positioned at a fill location, (iii) automatically transversely separating the first 20 and second 30 layers of the leading pouch 101 along the second end 114 of the leading pouch 101 so as to open the second end 114 of the leading pouch 101, (iv) placing a medical device 200 within the retention chamber 119 defined by the leading pouch 101 through the open second end 114 of the leading pouch 101, (v) sealing the second end 114 of the leading pouch 101 with the medical device 200 retained within the retention chamber 119, (vi) automatically detaching the leading pouch 101 from the trailing pouch 102 along the line of weakness 41 in the first layer 20 between the leading pouch 101 and the immediately trailing pouch 102, and (vii) repeating steps (ii) through (vi) for subsequent pouches 100 in the web 10.

The first embodiment of the second aspect of the invention can be conveniently performed utilizing any of the commercially available packaging machines designed for the automated packaging of goods into standard polyethylene and polypropylene bags using a continuous web of such bags. Examples of such machines include the HS-100 Excel, H-100, HB-85, HB-65, HB-55 and HB-25 Autobag® systems available from Automated Packaging Systems, Inc. of Streetsboro, Ohio; the BPS1, BPS2 and the SideKick systems available from Sharp Packaging of Sussex, Wis., and the TL-1000 system available from Advanced Poly Packaging of Akron, Ohio. Such systems may require some modifications in order to properly feed and seal the breather pouches 100 of the present invention as the handling of TYVEK® is substantially different that the handling and tearing characteristics of polyethylene and polypropylene for which such machines were designed. Exemplary modifications may include the use of feed rollers (not shown) with an increased tack in order to prevent the TYVEK® face of the pouches 100 from machine direction slippage or cross-direction wandering, and replacement of the standard heat sealing bar (not shown) with a heat sealing bar capable of providing the necessary ⅜ inch wide microbial barrier seal.

The first embodiment of the second aspect conveys the continuous web 10 to the fill location from above the fill location (i.e., a top-feed method). The commercially available automatic packaging machines disclosed above include the electronic sensors, electrical controls and mechanical systems necessary for automatically achieving steps (ii) and (iii) of the process (i.e., conveying the web 10 in a machine direction x until the leading pouch 101 is positioned at a fill location and automatically transversely separating the first 20 and second 30 layers of the leading pouch 101 along the second end 114 of the leading pouch 101 so as to open the second end 114 of the leading pouch 101).

A medical device 200 is then placed, typically by hand, within the retention chamber 119 of the leading pouch 101 through the open second end 114 of the leading pouch 101. Certain medical devices 200 may be susceptible to automatic loading of the medical device 200 into the leading pouch 101 using automatic loading equipment such as vibratory bowl feeders such as the Accu-Count® Advantage, Accu-Count® 107, 118 and 124, and Dac-1000 available from Automated Packaging Systems, Inc. of Streetsboro, Ohio; semi-automatic scales such as the Accu-Scale® 200 available from Automated Packaging Systems, Inc. of Streetsboro, Ohio; and conveyor systems such as the Maximizer® available from Automated Packaging Systems, Inc. of Streetsboro, Ohio.

The commercially available automatic packaging machines disclosed above and modified as necessary, also include the electronic sensors, electronic controls and mechanical systems necessary for automatically achieving steps (v) and (vi) of the process (i.e., sealing the second end 114 of the leading pouch 101 with the medical device 200 retained within the retention chamber 119, and automatically detaching the leading pouch 101 from the trailing pouch 102 along the lines of weakness 41 in the first 20 layer between the leading pouch 101 and the immediately trailing pouch 102). Of course, the line of weakness 41 in the first layer 20 must be configured and arranged with a tear strength suited to the specific machine employed.

A second embodiment of the second aspect of the invention uses the second embodiment of the first aspect of the invention (i.e., a side-feed continuous web 10).

The second embodiment of the second aspect of the invention includes the steps of (i) obtaining a side-feed web 10 of breather pouches 100, (ii) automatically conveying the web 10 in a machine direction x until the leading pouch 101 is positioned at a fill location, (iii) automatically transversely separating the first 20 and second 30 layers of the web 10 along the first lateral side 11 of the web 10 so as to provide access to the retention chamber 119 defined by the leading pouch 101 through the first lateral side 11 of the web 10, (iv) placing a medical device 200 within the retention chamber 119 defined by the leading pouch 101 through the first lateral side 11 of the web 10, (v) sealing the leading pouch 101 along the first lateral side 11 of the web 10 to form a seal line 124 with the medical device 200 retained within the retention chamber 119, (vi) trimming the processing margin 50 from the web 10 along a trim line (not shown) located between the seal line 124 and the first lateral side 11 of the web 10 so as to define the second end 114 of the leading pouch 101, (vii) automatically detaching the leading pouch 101 from the trailing pouch 102 along the line of detachment 40 between the leading pouch 101 and the immediately trailing pouch 102, and (viii) repeating steps (ii) through (vii) for subsequent pouches 100 in the web 10.

The second embodiment of the second aspect of the invention can be conveniently performed utilizing any of the commercially available packaging machines designed for the automated packaging of goods into standard polyethylene and polypropylene bags using a continuous web of such bags. Examples of such machines include the Sprint® SP-100V and SP-100H systems available from Automated Packaging Systems, Inc. of Streetsboro, Ohio. Such systems may require some modifications in order to properly feed and seal the breather pouches 100 of the present invention as the handling of TYVEK® is substantially different that the handling and tearing characteristics of polyethylene and polypropylene for which such machines were designed. Exemplary modifications may include the use of gripper belts (not shown) with an increased tack in order to prevent the TYVEK® face of the pouches 100 from machine direction slippage, and replacement of the standard heat sealing bar (not shown) with a heat sealing bar capable of providing the necessary 3/8 inch wide microbial barrier seal.

The second embodiment of the second aspect conveys the continuous web 10 to the fill location from a horizontal side of the fill location (i.e., a side-feed method). The commercially available automatic packaging machines disclosed above include the electronic sensors, electronic controls and mechanical systems necessary for automatically achieving steps (ii) and (iii) of the process (i.e., conveying the web 10 in a machine direction x until the leading pouch 101 is positioned at a fill location, and automatically transversely separating the first 20 and second 30 layers of the web 10 along the first lateral side 11 of the web 10 so as to provide access to the retention chamber 119 defined by the leading pouch 101). Step (iii) will typically be accompanied by the step of either automatically detaching the first 20 and second 30 layers along the line of attachment 51, or slitting the second layer 30 within the processing margin 50.

A medical device 200 is then placed, typically by hand, within the retention chamber 119 of the leading pouch 101 through the open second end 114 of the leading pouch 101. Certain medical devices 200 may be susceptible to automatic loading of the medical device 200 into the leading pouch 101 using automatic loading equipment including vibratory bowl feeders such as the Accu-Count® Advantage, Accu-Count® 107, 118 and 124, and Dac-1000 available from Automated Packaging Systems, Inc. of Streetsboro, Ohio.

The commercially available automatic packaging machines disclosed above and modified as necessary, include the electronic sensors, electronic controls and mechanical systems necessary for automatically achieving steps (v) through (vii) of the process (i.e., sealing the leading pouch 101 along the first lateral side 11 of the web 10 with the medical device 200 retained within the retention chamber 119, trimming the processing margin 50 from the web 10 along a trim line (not shown) and automatically detaching the leading pouch 101 from the trailing pouch 102 along the lines of weakness 41 and 42" in the first 20 and second 30 layers between the leading pouch 101 and the immediately trailing pouch 102). The lines of weakness 41 and 42" in the first 20 and second 30 layers must be configured and arranged with tear strengths suited to the specific machine employed.

I claim:

1. An article of commerce comprising:
    (a) a longitudinally continuous web having a longitudinal down-web direction, a lateral cross-web direction, and lateral sides, with:
        (i) superimposed first and second layers secured together by spaced apart lateral seals and longitudinal seals spaced along each longitudinal edge of the web; wherein:
            (A) the first layer comprises a gas permeable microbial barrier layer, and
            (B) the second layer comprises a thermoplastic gas impermeable layer,
        (ii) longitudinally spaced laterally extending lines of weakness in one of the first or second layer said lines of weakness being adjacent to one of said lateral seals,
        (iii) longitudinally spaced laterally extending lines of separation in the other first or second layer with the lines of separation paired with the lines of weakness wherein upon detachment of the web along the line of weakness access is created to a space between the first layer and the second layer on a first side of the line of weakness while maintaining the adjacent seal along a second side of the line of weakness; and,
    (b) the seals between the layers being peelable seals delineating sides and an end of the space between the first and second layer for receiving a product to be sterilized by sterilizing gas passed through the permeable layer.

2. The article of claim 1 wherein the lines of weakness are in the first layer and the lines of separation are in the second layer.

3. The article of claim 2 wherein the lines of weakness are lines of perforation with a hole:land area ratio of about 15:1 to 25:1 with about 0.4 to 0.6 perforations per centimeter.

4. The article of claim 1 wherein the lines of weakness are in the second layer and the lines of separation are in the first layer.

5. The article of claim 1 wherein the longitudinally continuous web forms a roll.

6. The article of claim 1 wherein the paired laterally extending lines of weakness and laterally extending lines of separation in the first and second layers are superimposed.

7. The article of claim 6 wherein the longitudinally continuous web is repetatively folded back at regular intervals along the superimposed paired laterally extending line of weakness and laterally extending line of separation to form a pleated stack.

8. The article of claim 1 wherein the first and second layers are sealed along the lateral sides with a peelable seal which is impervious to microbes.

9. The article of claim 1 wherein the first layer is a thermoplastic gas permeable microbial barrier.

10. The article of claim 9 wherein the first layer is a spunbonded olefin gas permeable microbial barrier.

11. The article of claim 1 wherein the second layer is transparent.

12. The article of claim 1 wherein the lines of weakness are lines of perforation.

13. An article of commerce comprising:
(a) a longitudinally continuous web having a longitudinal down-web direction, a lateral cross-web direction, and lateral ends; with:
   (i) superimposed first and second layers being sealed together by seals along one lateral end and along spaced side portions, wherein:
      (A) the first layer comprises a gas permeable microbial barrier layer, and
      (B) the second layer comprises a thermoplastic gas impermeable layer,
   (ii) a longitudinally spaced series of paired laterally extending lines of weakness and septeration in the first and second layers,
   (iii) wherein the first and second layers are sealed along a pair of laterally extending seal lines located proximate each paired lines of weakness and separation with the individual laterally extending seal lines in each pair of laterally extending seal lines separated by a paired lines of weakness and separation wherein upon detachment of the web along the line of weakness access is created to a space between the first layer and the second layer on a first side of the line of weakness while maintaining the adjacent seal along a second side of the line of weakness and,
(b) the seals between the layers being peelable seals delineating sides and an end of the space between the first and second layer to receive a product to be sterilized by sterilizing gas passed through the permeable layer.

14. The article of claim 13 wherein the longitudinally continuous web forms a roll.

15. The article of claim 13 wherein the paired laterally extending lines of weakness in the first and second layers are superimposed.

16. The article of claim 15 wherein the longitudinally continuous web is repetatively folded back at regular intervals along the superimposed paired laterally extending line of weakness and laterally extending line of separation to form a pleated stack.

17. The article of claim 13 wherein the first layer is a thermoplastic gas permeable microbial barrier.

18. The article of claim 17 wherein the first layer is a spunbonded olefin gas permeable microbial barrier.

19. The article of claim 13 wherein the second layer is transparent.

20. The article of claim 13 wherein the line weakness is a line of perforations in the first layer which line has a hole:land area ratio of about 15:1 to 50:1 with about 0.2 to 0.6 perforations per centimeter.

21. An article of commerce comprising:
(a) a longitudinally continuous web having a longitudinal down-web direction, a lateral cross-web direction, and lateral sides, with:
(b) superimposed first and second layers sealed together along the longitudinal sides and having spaced apart sealed lateral sides to define bags for packaging sterilizable items, wherein both the first and second layers are effective for preventing passage of microbes through the layer and at least the first layer is effective for permitting the passage of a sterilization gas,
(c) longitudinally spaced laterally extending lines of weakness in one of the first and second layers said lines of weakness being adjacent to one of said lateral seals,
(d) longitudinally spaced laterally extending lines of separation in the other of the first and second layers with the lines of separation paired with the lines of weakness wherein upon detachment of the web along the line of weakness, access is created to a space between the first layer and the second layer on a first side of the line of weakness while maintaining the adjacent seal along a second side of the line of weakness; and,
(e) the seals between the layers being peelable to fully separate the layers one from the other whereby to facilitate sterile access to items packaged in such bags without fear of contamination by residue from either layer.

22. The article of claim 21 wherein the first layer defines a surface area and the entire surface area of the first layer is effective for preventing passage of microbes through the layer and permitting the passage of a sterilization gas.

23. A web for making sterilizable packages comprising:
a) an elongate strip of plastic material forming backs of a number of bags;
b) the plastic strip being impervious to microbes and sterilizing gasses;
c) pieces of microbial barrier material forming face layers, one for each of the bags, the barrier material being impervious to microbes and permeable to sterilizing gasses;
d) seals between the strips and the pieces to delineate individual bags each sealed at the sides and bottom and each with a top opening for the insertion of a sterilizable product;
e) each of the seals being fully peelable whereby products sequentially inserted into the bags and packaged by heat sealing to close the openings in the bags may be sterilized and subsequently accessed with out fear of contamination by residues of a package resulting from such package being opened; and,
f) spaced lines of weakness each in the strip adjacent to said bottom seal wherein upon detachment of the bag from the web along the line of weakness access is created to a bag on a first side of the line of weakness and a seal is maintained on a second side of the line of weakness, said line of weakness delineating bag ends and provides for facile separation of the bags, one from another.

24. The web of claim 23 wherein the barrier material is a spun bonded polyolefin material.

25. The web of claim 23 wherein the lines pf weakness are lines of perforations with a hole:land area ratio of about 15:1 to 25:1 with about 0.4 to 0.6 perforations per centimeter.

* * * * *